(12) United States Patent
Maschke

(10) Patent No.: US 6,263,043 B1
(45) Date of Patent: Jul. 17, 2001

(54) MEDICAL EXAMINATION SYSTEM ALLOWING MR IMAGES AND X-RAY EXPOSURES TO BE MADE WITHOUT RE-SITUATING A PATIENT ON A PATIENT BED

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/150,022

(22) Filed: Sep. 9, 1998

(30) Foreign Application Priority Data

Sep. 15, 1997 (DE) .............................. 197 40 533

(51) Int. Cl.$^7$ ................................. G01N 23/04
(52) U.S. Cl. ................ 378/63; 600/415; 378/209; 378/181
(58) Field of Search ................... 600/415, 411; 378/63, 181, 204, 209

(56) References Cited

U.S. PATENT DOCUMENTS

| | | | |
|---|---|---|---|
| 4,247,778 | * | 1/1981 | Waerve .............................. 378/177 |
| 5,497,408 | * | 3/1996 | Kayser .............................. 378/177 |
| 5,807,254 | * | 9/1998 | Meulenbrugge et al. . |
| 5,818,901 | * | 10/1998 | Schulz . |

FOREIGN PATENT DOCUMENTS

| | | |
|---|---|---|
| 39 31 531 | 4/1990 | (DE) . |
| WO 96/00520 | 1/1996 | (WO) . |

* cited by examiner

*Primary Examiner*—David P. Porta
*Assistant Examiner*—Pamela R. Hobden
(74) *Attorney, Agent, or Firm*—Schiff Hardin & Waite

(57) ABSTRACT

A medical examination system which allows the production of x-ray exposures in the context of an MR examination without re-situating the patient has a solid-state radiation detector integrated in the patient bed of an MR apparatus, and an adjustably mounted x-ray source with the further x-ray system components being allocated thereto.

3 Claims, 3 Drawing Sheets

MEDICAL EXAMINATION SYSTEM ALLOWING MR IMAGES AND X-RAY EXPOSURES TO BE MADE WITHOUT RE-SITUATING A PATIENT ON A PATIENT BED

BACKGROUND OF THE INVENTION

1. Field of the Invention

The present invention is directed to a medical examination apparatus of the type wherein both magnetic resonance (MR) images and x-ray exposures of a patient are made.

2. Description of the Prior Art

Magnetic resonance (MR) is a proven diagnosis method that enables tomograms and three-dimensional reconstructions. The examination time, however, is relatively long and lies in the order of magnitude of several minutes. For specific examinations, for example of the skull, thorax, abdomen or mammaries, it is meaningful to produce an x-ray exposure before and/or during the MR examination for shortening the exposure time and/or for planning the further execution of the MR examinations. The diagnosis quality is additionally enhanced as a result. German OS 39 31 531 discloses a medical examination system having an MR apparatus and an x-ray exposure device, wherein the image data are superimposed for improving the diagnosis or are individually, i.e. separately, presented. Two individual pick-up devices having two individual support devices for the patient are provided.

SUMMARY OF THE INVENTION

An object of the present invention is to provide a medial diagnostic installation wherein x-ray exposures of a patient disposed in an MR apparatus can also be prepared without re-situating the patient on the patient bed.

This object is inventively achieved in a medical diagnostic installation having an MR apparatus into and out of which a patient is moved on a patient bed, and an x-ray source positionable above the bed outside of the MR apparatus, and a solid-state detector on formed by a matrix of amorphous silicon detector elements, which is insensitive to magnetic fields, arranged in the patient bed for the preparation of x-ray exposures. The detector can be displaceably mounted within the bed in order to enable the exposure of different body regions. A ceiling stand for the x-ray source can be provided for the producing x-ray exposures.

The operation (starting the MR sequences, triggering the radiation for the x-ray system, image optimization, image compilation and printout of the images) of the MR system and of the digital x-ray system can ensue at a common work station that simultaneously serves the purpose of observing the registered images.

DESCRIPTION OF THE PREFERRED EMBODIMENTS

Figure 1:
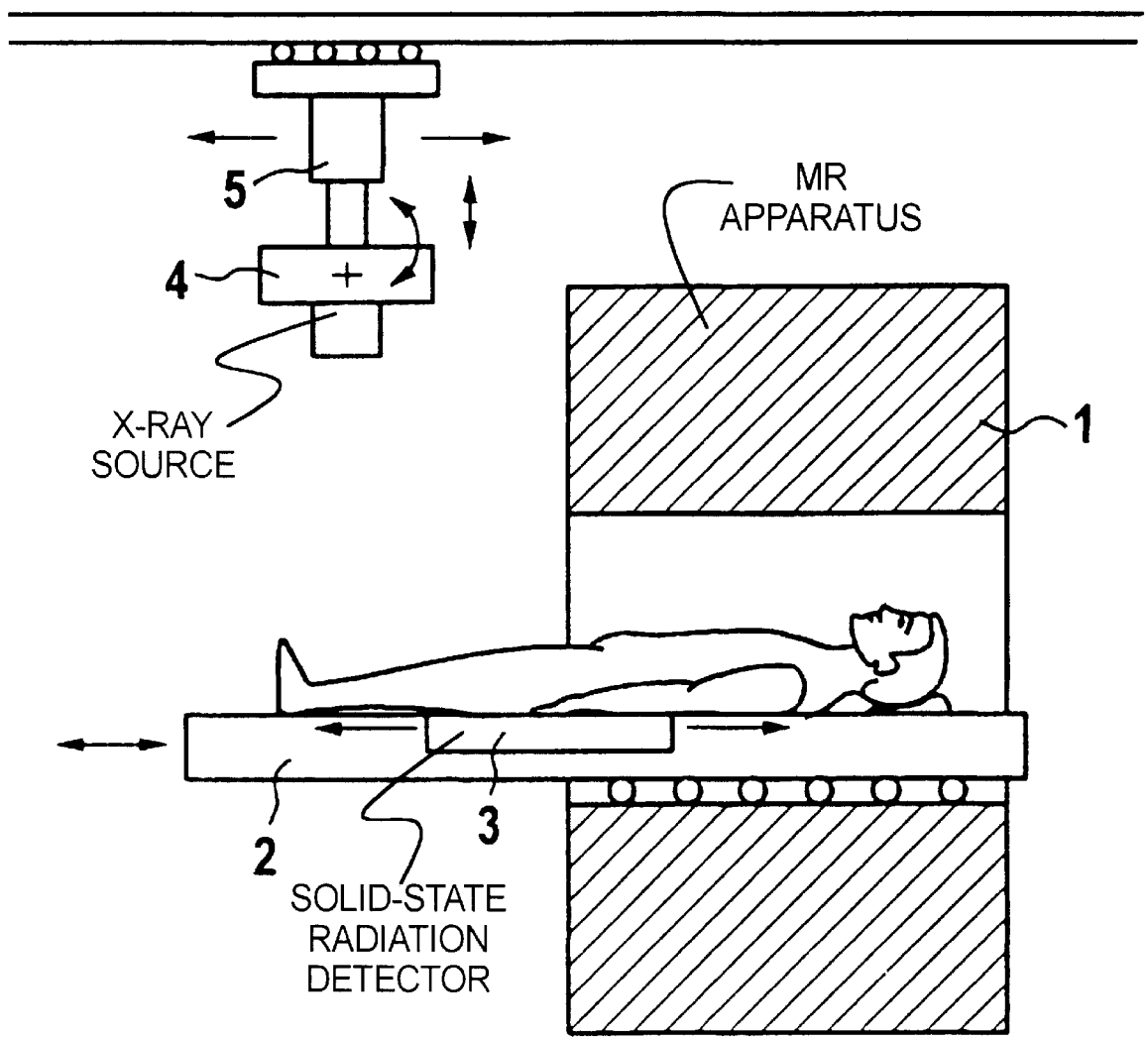
FIGS. 1 through 3 illustrate a medical examination system of the invention with various patient positions.
Figure 2:
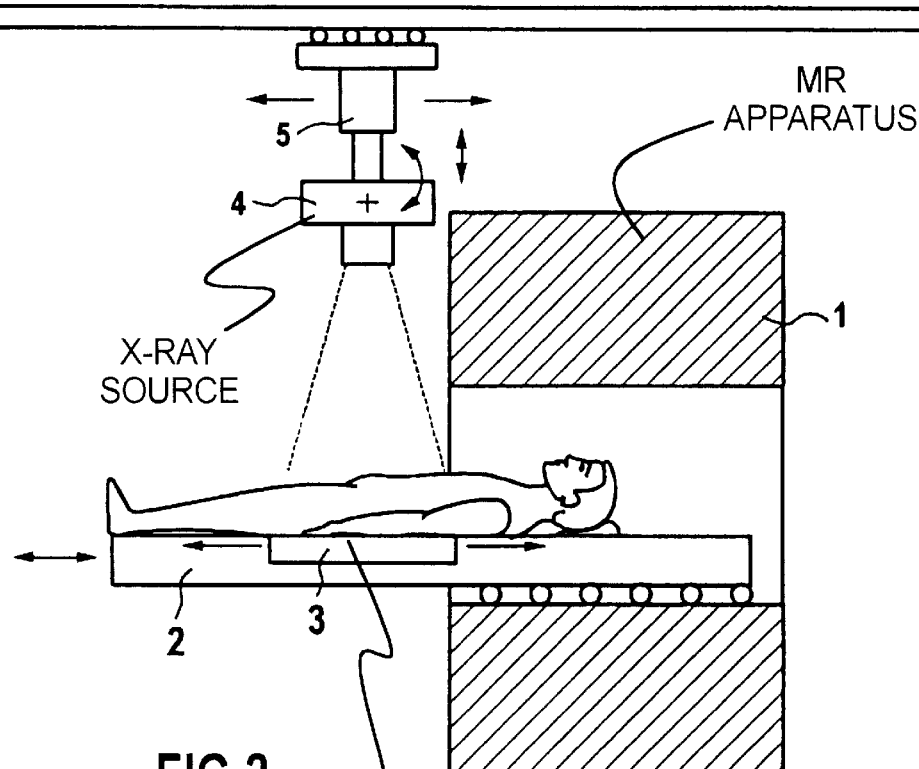
Figure 3:
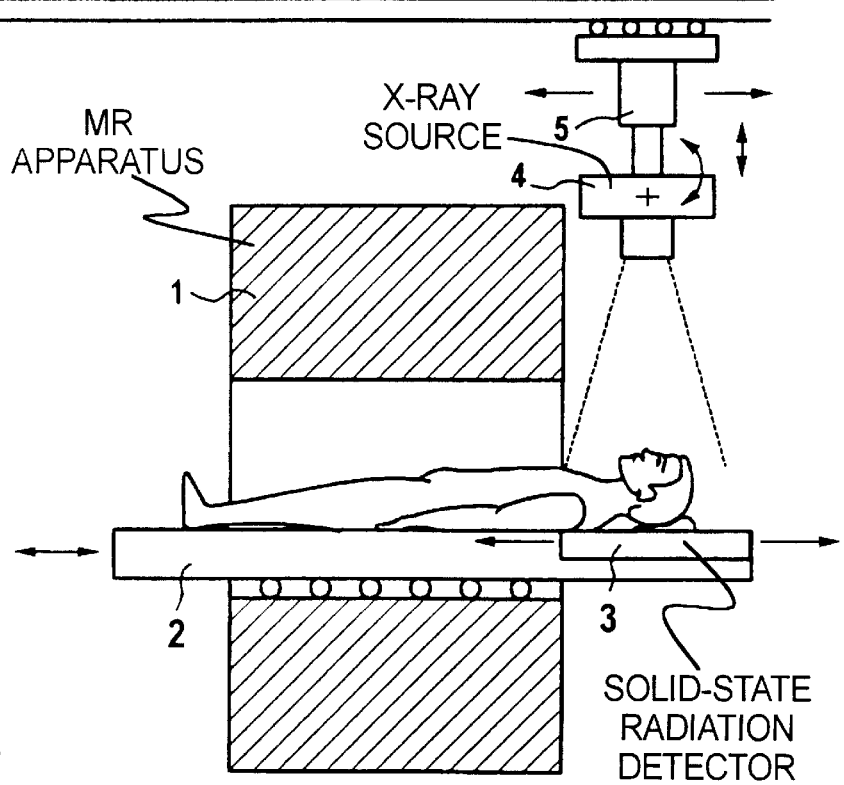

FIGS. 1 through 3 schematically show an MR apparatus 1 with a patient bed 2. The patient bed 2 is arranged in the inside of the MR apparatus 1 so as to be displaceable in the longitudinal direction thereof. A digital radiation detector 3 for the preparation of digital x-ray exposures is displaceably mounted in the bed 2. The radiation detector 3 is non-magnetic, so it does not interfere with the preparation of MR exposures. The detector 3 is preferably a solid-state detector formed by a matrix of amorphous silicon detector elements. For generating the x-rays, an x-ray source 4 is height-adjustably seated at a ceiling stand 5. The ceiling stand 5 is displaceable at the ceiling.

FIG. 2 shows a position of the components 2 through 5 in which an x-ray exposure of the abdomen is made.

FIG. 3 shows the position of the components 2 through 5 for the preparation of an x-ray skull exposure.

The MR apparatus 1 can be an open system with lateral access to the patient, or a closed system or a system with two parts arranged axially spaced from one another between which access to the patient is possible (interventional MR system). It is thereby possible, for example to prepare a lung exposure by applying the x-rays between these parts.

Figure 4:
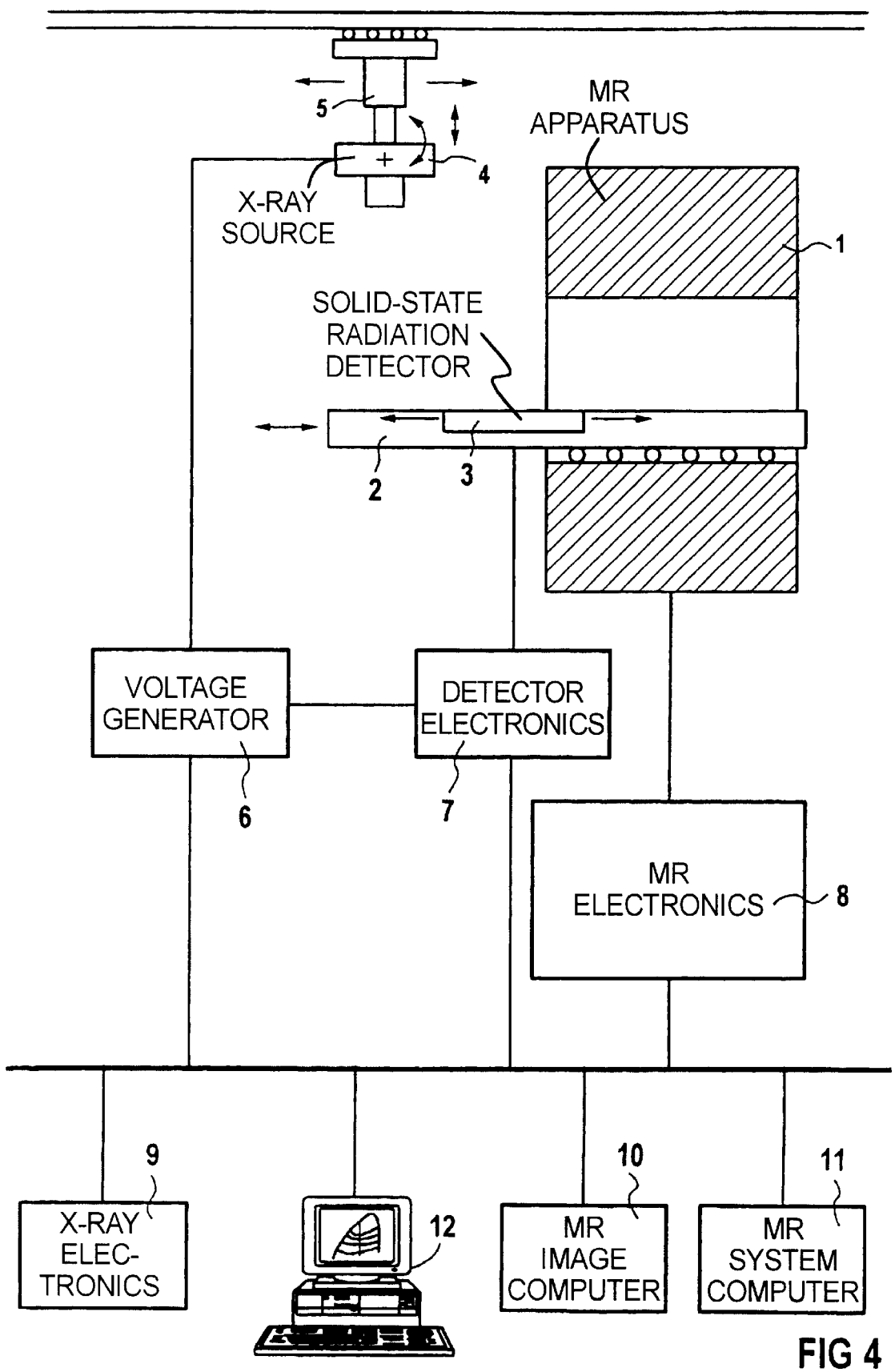
FIG. 4 is a block circuit diagram for the examination system according to FIGS. 1–3.

FIG. 4 shows a block circuit diagram of the illustrated medical examination system having a voltage generator 6, detector electronics 7 for the detector control and image preparation, MR electronics 8 for control, pre-amplification, generation and modulation of the RF signals and for gradient control, an x-ray electronics 9, an MR image computer 10 and an MR system computer 11. An operating counsel 12 is also provided for the playback of the MR image and the x-ray image on a diagnosis monitor for MR and x-ray examination.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical examination system comprising:

a magnetic resonance imaging apparatus having a patient bed adapted to receive a patient for producing a magnetic resonance image of the patient while the patient is in a magnetic resonance imaging position on the patient bed, said patient bed being movable into and out of an examination volume of said magnetic resonance apparatus;

an x-ray source disposed for irradiating a patient on said patient bed when said patient bed is moved out of said examination volume; and a solid-state radiation detector contained in said patient bed for detecting x-rays from said x-ray source attenuated by said patient without re-situating said patient from said magnetic resonance imaging position on said patient bed.

2. A medical examination system as claimed in claim 1 wherein said solid-state detector is displaceably mounted within said patient bed.

3. A medical examination system as claimed in claim 1 wherein said x-ray source and said solid-state radiation detector comprise an x-ray system, and said medical examination system comprising a common operating console for operating both said magnetic resonance imaging apparatus and said x-ray system.

* * * * *